(12) United States Patent
Ferrari et al.

(10) Patent No.: US 9,060,999 B2
(45) Date of Patent: *Jun. 23, 2015

(54) ELLAGITANNINS RICH EXTRACTS COMPOSITION

(71) Applicant: Horphag Research IP (QR) LTD, Limassol (CY)

(72) Inventors: Victor Ferrari, Cointrin (CH); Frank Schoenlau, Münster (DE); Carolina Burki, Cointrin (CH)

(73) Assignee: HORPHAG RESEARCH IP (QR) LTD, Limassol (CY)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,385

(22) PCT Filed: Dec. 21, 2012

(86) PCT No.: PCT/EP2012/076845
§ 371 (c)(1),
(2) Date: Jun. 18, 2014

(87) PCT Pub. No.: WO2013/093102
PCT Pub. Date: Jun. 27, 2013

(65) Prior Publication Data
US 2014/0322369 A1    Oct. 30, 2014

(30) Foreign Application Priority Data
Dec. 23, 2011 (CH) ........................ 2045/11

(51) Int. Cl.
| | | |
|---|---|---|
| *A61K 36/40* | (2006.01) | |
| *A61K 36/49* | (2006.01) | |
| *A61K 36/44* | (2006.01) | |
| *A61K 31/357* | (2006.01) | |
| *A61K 31/7024* | (2006.01) | |
| *A61K 45/06* | (2006.01) | |
| *A61K 31/365* | (2006.01) | |
| *A23L 1/30* | (2006.01) | |

(52) U.S. Cl.
CPC ............ *A61K 31/357* (2013.01); *A61K 31/7024* (2013.01); *A61K 36/49* (2013.01); *A61K 45/06* (2013.01); *A61K 31/365* (2013.01); *A23L 1/3002* (2013.01); *A23V 2002/00* (2013.01)

(58) Field of Classification Search
CPC ...................................................... A61K 36/49
See application file for complete search history.

(56) References Cited

U.S. PATENT DOCUMENTS

| 8,372,454 B2 | 2/2013 | Aviram et al. |
| 2004/0247698 A1 | 12/2004 | Valenzuela Cortes |

FOREIGN PATENT DOCUMENTS

| WO | WO-2011/161655 A1 | 12/2011 |
| WO | WO 2011161655 A1 * | 12/2011 |

OTHER PUBLICATIONS

Bhattacharya, D. (2011) "Fight Malaria at home: Therapeutic and prophylaxis clinical data", *Asian Pacific Journal of Tropical Disease*, 1(2): 142-149.
International Preliminary Report on Patentability dated Apr. 2, 2014 issued in PCT Application No. PCT/EP2012/076837.
International Preliminary Report on Patentability dated Apr. 22, 2014 issued in PCT Application No. PCT/EP2012/076845.
International Search Report dated Apr. 11, 2013 issued in PCT Application No. PCT/EP2012/076837.
International Search Report dated Apr. 16, 2013 issued in PCT Application No. PCT/EP2012/076845.
Khallouki, F., et al. (2007) "Isolation, purification and identification of ellagic acid derivatives, catechins, and procyanidins from the root bark of *Anisophyllea dichostyla* R. Br", *Food Chem Toxicol*, 45(3): 472-485.
Larrosa, M., et al. (2010) "Ellagitannins, ellagic acid and vascular health", *Molecular Aspects of Medicine*, 31(6):513-539.
Written Opinion of the International Preliminary Examining Authority dated Nov. 19, 2013 issued in PCT Application No. PCT/EP2012/076837.
Office Action dated Oct. 28, 2014 issued in U.S. Appl. No. 14/366,386.
Raskin, I., et al. (2004) "Can an apple a day keep the doctor away?", *Current Pharmaceutical Design*, 10:3419-3429.
Revilla, E., et al. (1998) "Comparison of several procedures used for the extraction of anthocyanins from red grapes", *J. Agric. Food Chem.*, 46:4592-4597.

* cited by examiner

*Primary Examiner* — Chris R Tate
*Assistant Examiner* — Russell Fiebig
(74) *Attorney, Agent, or Firm* — Harness, Dickey & Pierce, P.L.C.

(57) ABSTRACT

The present invention relates to a composition consisting of ellagitannins rich extracts originated from plant extracts of the Fagaceae family, for use in a method for preventing or treating sleep and anxiety disorders, fatigue as well as for improving mood, reducing tension and raising energy in a subject.

17 Claims, No Drawings

ELLAGITANNINS RICH EXTRACTS COMPOSITION

PRIORITY STATEMENT

This application is a national stage application under 35 U.S.C. §371 of PCT International Application No. PCT/EP2012/076845, which has an international filling date of 21 Dec. 2012 and claims priority under 35 U.S.C. §119 to Switzerland Application No. 02045/11 filed 23 Dec. 2011. The contents of each application recited above are incorporated herein by reference in their entirety.

FIELD OF THE INVENTION

The present invention relates to a composition consisting of ellagitannins rich extracts originated from plant extracts of the Fagaceae family, for use in a method for preventing or treating fatigue, sleep disorders, anxiety, improving mood and raising energy in a subject.

BACKGROUND OF THE INVENTION

A mood is an emotional state. Moods differ from emotions in that they are less specific, less intense, and less likely to be triggered by a particular stimulus or event. Moods generally have either a positive or negative valence. In other words, people typically speak of being in a good mood or a bad mood.

Mood also differs from temperament or personality traits which are even longer lasting. Nevertheless, personality traits such as optimism and neuroticism predispose certain types of moods. Long term disturbances of mood such as depression and bipolar disorder are considered mood disorders. Mood is an internal, subjective state, but it often can be inferred from posture and other behaviors. One can be sent into a mood by an unexpected event, from the happiness of seeing an old friend to the anger of discovering betrayal by a partner. One may also just fall into a mood. Research also shows that a person's mood can influence how they process advertising. Further mood has been found to interact with gender to affect consumer processing of information.

Lack of Sleep

Sleep is a major factor in the mood. If one is sleeping deprived you could become more irritable, angry, more prone to stress, and less energized throughout the day. "Studies have shown that even partial sleep deprivation has a significant effect on mood. University of Pennsylvania researchers found that subjects who were limited to only 4.5 hours of sleep a night for one week reported feeling more stressed, angry, sad, and mentally exhausted. When the subjects resumed normal sleep, they reported a dramatic improvement in mood".

Medical Conditions

Depression, chronic stress, bipolar disorder, etc. are considered "mood disorders". It has been suggested that such disorders result from chemical imbalances in the brain's neurotransmitters, however some research challenges this hypothesis.

Negative Mood

Like positive moods, negative moods have important implications for human mental and physical wellbeing. Moods are basic psychological states that can occur as a reaction to an event or can surface for no apparent external cause. Since there is no intentional object that causes the negative mood, it has no specific start and stop date. It can last for hours, days, weeks, or longer. Negative moods can manipulate how individuals interpret and translate the world around them, and can also direct their behavior.

Negative moods can affect an individual's judgment and perception of objects and events. In a study done by Niedenthal and Setterlund (1994), research showed that individuals are tuned to perceive things that are congruent with their current mood. Negative moods, mostly low-intense, can control how humans perceive emotion-congruent objects and events and tend to affect their judgments and perceptions. These negative moods may lead to problems in social relationships. For example, one maladaptive negative mood regulation is an overactive strategy in which individuals over dramatize their negative feelings in order to provoke support and feedback from others and to guarantee their availability. A second type of maladaptive negative mood regulation is a disabling strategy in which individuals suppress their negative feelings and distance themselves from others in order to avoid frustrations and anxiety caused by others' unavailability.

Negative moods have been connected with depression, anxiety, aggression, poor self-esteem, physiological stress and decrease in sexual arousal. Negative moods are labeled as nonconstructive because it can affect a person's ability to process information. This can lead to problems in social relationships with others. Negative moods, such as anxiety, often lead individuals to misinterpret physical symptoms.

Positive Mood

Positive mood can be caused by many different aspects of life as well as have certain effects on people as a whole. Good mood is usually considered a state without an identified cause; people cannot pinpoint exactly why they are in a good mood. People seem to experience a positive mood when they have a clean slate, have had a good night sleep, and feel no sense of stress in their life.

"Generally, positive mood has been found to enhance creative problem solving and flexible yet careful thinking". "There have been many studies done on the effect of positive emotion on the cognitive mind and there is speculation that positive mood can affect people minds in good or bad ways. Some studies had stated that positive moods let people think creatively, freely, and be more imaginative. People in a positive mood are usually easier to talk to and want to have longer conversations compared to someone who is in a negative or neutral mood. Lastly positive mood can help people in situations where heavy thinking and brainstorming is involved. Positive mood has also been proven to show negative effects on cognition as well. According to the article "Positive mood is associated with implicit use of distraction". "There is also evidence that individual in positive moods show disrupted performance, at least when distracting information is present". The article states that other things in their peripheral views can easily distract people who are in good moods. The study is basically stating that it would be harder for positive moods to focus on the task at hand. In particular, happy people may be more sensitive to the hedonic consequences of message processing than sad people. Thus, positive moods are predicted to lead to decreased processing only when thinking about the message is mood threatening. In comparison, if message processing allows a person to maintain or enhance a pleasant state then positive moods need not lead to lower levels of message scrutiny than negative moods. It is assumed that initial information regarding the source either confirms or disconfirms mood-congruent expectations. Specifically, a positive mood may lead to more positive expectations concerning source trustworthiness or likability than a negative mood. As a consequence, people in a positive mood should be more surprised when they encounter an untrustworthy or dislikable source rather than a trustworthy or likable source.

While numerous antidepressant drugs are currently available and are partially effective, most fail to produce remission in a significant fraction of patients. This lack of adequately efficacious antidepressants may be due to our present inadequate understanding of the underlying pathophysiology and neurobiology of major depression.

A number of drugs and procedures have been developed to overcome some of these difficulties. These include ketamine (Zarate, et al., Arch Gen Psychiatry 2006; 63: 856-864), 5HT4 receptor agonists (Lucas, et al, Neuron, 2007; 55: 712-725), deep brain stimulation (Mayberg, et al, Neuron 2005; 45: 65 1 -660, 2005), agomelatin ( asper, et al., World J Biol Psychiatry 2009; 10: 1 17-126), and antagonists of CRF (Zoumakis, et al, Ann N Y Acad Sci 2006; 1083: 239-251), N 1 (Ebner, et al, Curr Pharm Dei 2009; 1 5: 1647-1674), kappa opioid (Carr, et al, Neuropsychopharmacology 2010; 35: 752-763) , and cholecystokinin (Smadja, et al, Psychopharmacology 1997; 132: 227-236) receptors. While some of these agents appear to have an increased speed of action, they may not possess greater efficacy and may have further limitations themselves in terms of degree of invasiveness, losses of efficacy with chronic administration, and dissociative side effects.

The family Fagaceae, or beech family, comprises about 900 species of both evergreen and deciduous trees and shrubs, which are characterized by alternate simple leaves with pinnate venation, unisexual flowers in the form of catkins, and fruit in the form of cup-like (cupule) nuts. Fagaceous leaves are often lobed and both petioles and stipules are generally present. Fruits lack endosperm and lie in a scaly or spiny husk that may or may not enclose the entire nut, which may consist of one to seven seeds. The best-known group of this family is the oaks, genus *Quercus*, the fruit of which is a non-valved nut (usually containing one seed) called an acorn. The husk of the acorn in most oaks only forms a cup in which the nut sits.

Several members of the Fagaceae have important economic uses. Many species of oak, chestnut, and beech (genera *Quercus, Castanea*, and *Fagus* respectively) are commonly used as timber for floors, furniture, cabinets, and wine barrels. Cork for stopping wine bottles and a myriad of other uses is made from the bark of cork oak, *Quercus suber*. Chestnuts, a tasty treat enjoyed by many in the winter, are the fruits from species of the genus *Castanea*. Numerous species from several genera are prominent ornamentals, and wood chips from the genus *Fagus* are often used in flavoring beers.

There is still a need for an effective, natural and safe composition for the prevention and/or treatment of fatigue, anxiety and sleep disorders, improving mood, reducing tension and raising energy in a subject.

SUMMARY OF THE INVENTION

In one aspect of the present invention there is provided a composition consisting of ellagitannins rich extracts originated from plant extracts of the Fagaceae family, for use in a method for preventing or treating fatigue, anxiety and sleep disorders, improving mood, reducing tensions (or stress) and raising energy in a subject.

In another aspect, the present invention provides for a dietary or food supplement, a food preparation, a beverage, a medicament and a topical preparation comprising the composition of the present invention.

Anxiety disorders and mood disorders are defined, for example, in the American Psychiatric Association: Diagnostic and Statistical Manual of Mental Disorders, Fourth Edition, Text Revision, Washington, D.C., American Psychiatric Association, 2000.

In some embodiments, the present invention provides a method of treating or preventing an anxiety disorder or mood disorder (such as any of those described herein), by administering to a mammal (including a human) the composition of the invention.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular form "a", "an" and "the" include plural references unless the context clearly dictates otherwise.

The term "extract", as used herein includes any preparation obtained from plants, fruits, roots or vegetables using an extraction method.

The term "food preparation" refers generally to material of either plant or animal origin, or of synthetic sources, that contain essential nutrients such as a carbohydrate, protein, fat, vitamin, mineral, etc. used in the body of an organism to sustain growth, repair, and vital processes and to furnish energy.

A "dietary or food supplement" refers to a product that contains substances like vitamins, minerals, foods, botanicals, amino acids and is intended to supplement the usual intake of these substances. Dietary supplements are found in pill, tablet, capsule, powder or liquid form and are meant to be taken by mouth.

The term "nutraceutical" refers to any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages. It also refers to a product isolated or purified from foods, and generally sold in medicinal forms not usually associated with food and demonstrated to have a physiological benefit or provide protection against diseases like chronic diseases for example.

The term "beverage" means a liquid for drinking, which may be water, flavored water, soft drinks, alcoholic drink, health drink, or an enriched drink like based on a diary product (milk) or fruit juice.

"Pharmaceutically acceptable excipients or carriers" are any materials that do not interfere with the pharmacological activity of the active ingredient(s) or degrade the body functions of the subject to which it can be administered but facilitate fabrication of dosage forms or administration of the composition. Examples of pharmaceutically acceptable excipient include but are not limited to maltodextrin, calcium phosphate, and fused silica. Pharmaceutically acceptable excipients also include flavorants, as well as various additives such as other vitamins and minerals, all solvents, dispersion media, coatings, isotonic and absorption delaying agents, sweeteners and the like, non-toxic auxiliary substances such as wetting or emulsifying agents, pH buffering agents and the like, such as for example, sodium acetate, sorbitan monolaurate, triethanolamine oleate, and inert ingredients such as talc and magnesium stearate which are standard excipients in the manufacture of tablets, capsules and other dosage forms.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and newborn subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

As used herein, the terms "prevention" and "preventing," when referring to a disorder or symptom, refers to a reduction in the risk or likelihood that a mammalian subject will develop said disorder, symptom, condition, or indicator after treatment according to the invention, or a reduction in the risk or likelihood that a mammalian subject will exhibit a recurrence of said disorder, symptom, condition, or indicator once a subject has been treated according to the invention and cured or restored to a normal state (e.g., placed in remission from a targeted anxiety, mood, fatigue, stress, energy and/or fatigue disorders).

As used herein, the terms "treatment" or "treating," when referring to mood, fatigue, stress, energy and/or fatigue disorders, refers to inhibiting or reducing the progression, nature, or severity of the subject condition or delaying the onset of the condition.

The composition of the invention consisting of ellagitannins rich extracts originated from plant extracts of the Fagaceae family is suitable for use in a method for preventing or treating sleep and anxiety disorders, fatigue as well as for improving or boosting mood, reducing tensions or stress and raising energy of a subject.

In mammals and birds, "sleep" is divided into two broad types: rapid eye movement (REM) and non-rapid eye movement (NREM or non-REM) sleep. Each type has a distinct set of associated physiological and neurological features. The American Academy of Sleep Medicine (AASM) further divides NREM into three stages: N1, N2, and N3, the last of which is also called delta sleep or slow-wave sleep (SWS).

During REM most muscles are paralyzed. REM sleep is turned on by acetylcholine secretion and is inhibited by neurons that secrete serotonin. This level is also referred to as paradoxical sleep because the sleeper, although exhibiting EEG waves similar to a waking state, is harder to arouse than at any other sleep stage. Vital signs indicate arousal and oxygen consumption by the brain is higher than when the sleeper is awakehttp://en.wikipedia.org/wiki/Sleep-cite_note-8. An adult reaches REM approximately every 90 minutes, with the latter half of sleep being more dominated by this stage. The function of REM sleep is uncertain but a lack of it will impair the ability to learn complex tasks. One approach to understanding the role of sleep is to study the deprivation of it. During this period, the EEG pattern returns to high frequency waves which look similar to the waves produced while the person is awake The terms "sleep disorders", or somnipathy, is a medical disorder of the sleep patterns of a person or animal subject. Some sleep disorders are serious enough to interfere with normal physical, mental and emotional functioning. Polysomnography is a test commonly ordered for some sleep disorders. At some time, most of the subjects have experienced trouble sleeping properly. However, if sleep problems are a regular occurrence and interfere with the daily life, one may be suffering from a sleep disorder. Sleep disorders cause more than just sleepiness. Poor quality sleep can have a negative impact on the energy, emotional balance, and health.

Disruptions in sleep can be caused by a variety of issues, from teeth grinding (bruxism) to night terrors. When a person suffers from difficulty in sleeping with no obvious cause, it is referred to as insomnia. In addition, sleep disorders may also cause sufferers to sleep excessively, a condition known as hypersomnia. Sleep can often be a barometer of the overall health. In many cases, people in good health tend to sleep well, whereas repeated sleeping problems may indicate an underlying medical or mental health problem, be it minor or serious. Sleeping well is essential to physical health and emotional well-being. Unfortunately, even minimal sleep loss can take a toll on the mood, energy, efficiency, and ability to handle stress.

There are more than 100 different sleeping and waking disorders. They can be grouped into four main categories:
Problems falling and staying asleep (insomnia)
Problems staying awake (excessive daytime sleepiness)
Problems sticking to a regular sleep schedule (sleep rhythm problem)
Unusual behaviors during sleep (sleep-disruptive behaviors)

Preferably, the composition of the invention may be used in a method for treating or preventing sleep disorders comprising insomnia, hypersomnia, sleep rhythm problem and/or sleep-disruptive behaviors.

In a further particular embodiment of the invention, the composition of the invention is used in a method for preventing or treating fatigue in a subject. Fatigue, or low perceived energy levels, is associated with various conditions such as exertion, inanition, or lack of sleep; an imbalanced or inappropriate diet; acute or chronic stressful states; and can be a concomitant of aging. The degree of an individual's fatigue varies with the causative factors and the duration they have been present. There is also a variance in how each individual person deals with or tolerates fatigue. Intense fatigue can produce physical and/or mental symptoms, negatively affecting one's abilities both during wakefulness and sleep.

By the term "fatigue" is intended, for the purpose of this invention, a "lack of energy", a "lack of vitality" or "weakness", either short term or persistent, including symptoms of the chronic fatigue syndrome that involve unrefreshing sleep, after any exertion, weariness that lasts for more than a day, fatigue that is not the result of excessive work or exercise, fatigue substantially impairs a person's ability to function normally at home, at work, and in social occasions. By the term "vitality", the invention refers to a healthy capacity for vigorous activity. Mild exercise often makes the symptoms; especially fatigue, much worse, sleep or rest does not relieve fatigue. Fatigue leads to physical symptoms that include sore throat, swollen lymph nodes in the neck or armpits, muscle pain, pain without redness or swelling in a number of joints, intense or changing patterns of headaches, short-term memory loss or a severe inability to concentrate that affects work, school, or other normal activities.

In this embodiment, the composition of the invention is preferably used in the prevention or the treatment of fatigue comprising the lack of energy, the lack of vitality or weakness.

According to the invention, "fatigue disorders" preferably comprises chronic fatigue syndrome or CSF. In 1994 an updated case definition was developed by an international working group of CFS experts. Although the criteria were designed to be used for research purposes, physicians utilize them as diagnostic guidelines for CFS.

A CSF questionnaire is illustrated in example 4. The case definition criteria, calls for four of eight symptoms to be present along with fatigue that interferes with physical, mental, social and educational activities. Both the fatigue and symptoms must have occurred for [at least] a six month period. People with CFS may experience many more than the eight symptoms named in the case definition, so knowledgeable physicians will take this fact into consideration when making a diagnosis (after other possible reasons for symptoms have been ruled out).

In this particular embodiment the composition of the invention is used in the prevention or the treatment of fatigue comprising the enhancement of the prevention, the treatment or the alleviation of fatigue disorders consisting of Chronic Fatigue Syndrome (CSF).

Everybody suffers from bad mood or mild depression sometimes but to get out of it is difficult. The composition of the invention is preferably used to improving or boosting mood and consequently presents direct or indirect effect on mood. By consuming the composition of the invention one can improve its mood as well as its energy levels. Without being bound by theory, the composition of the invention provides a feel-good brain chemical and thereby boosts mood.

In a particular embodiment of the invention, the composition of the invention is used to enhance the vigour and mood states of a mammal, preferably a Human. As used herein the term "vigour" means active bodily or mental strength or force. Vigour is also intensity of action or effect and is evidenced by active, healthy, well balanced mental and physical states. Feelings of vigour or fatigue can be assessed through a Profile of Mood States questionnaire (POMS) (McNair D M, Lorr M, Droppleman L F "EdITS manual for the Profile of Mood States" San Diego: Calif.: EdITS Educational & Industrial Testing Service; 1992). The POMS questionnaire has been validated as a method to determine significant differences in subjective feelings subject while undergoing a clinical trial.

In this particular embodiment, the composition of the invention is preferably used in the improvement of mood comprising the enhancement of the vigour, the alleviation of negative mood and the stimulation or boosting of positive mood (as defined above). For example, "negative moods" have been connected with depression, anxiety, aggression, poor self-esteem, physiological stress and decrease in sexual arousal. Negative moods are labeled as nonconstructive because it can affect a person's ability to process information. This can lead to problems in social relationships with others. Negative moods, such as anxiety, often lead individuals to misinterpret physical symptoms.

In the opposite, good or "positive mood" is usually considered a state without an identified cause; people cannot pinpoint exactly why they are in a good mood. People seem to experience a positive mood when they have a clean slate, have had a good night sleep, and feel no sense of stress in their life. Generally, positive mood has been found to enhance creative problem solving and flexible yet careful thinking According to a preferred embodiment of the invention, the composition of the invention is used in a method for preventing or treating anxiety disorders and/or mood disorders of a mammal, preferably a Human.

Anxiety disorders and mood disorders are defined, for example, in the American Psychiatric Association: Diagnostic and Statistical Manual of Mental Disorders, Fourth Edition, Text Revision, Washington, D.C., American Psychiatric Association, 2000.

"Anxiety disorder" is a persistent fear of social or performance situations that might involve exposure to unfamiliar people or possible scrutiny by others. Many forms and symptoms may include: overwhelming feelings of panic and fear, uncontrollable obsessive thoughts, painful, intrusive memories, recurring nightmares, and even physical symptoms such as feeling sick to your stomach, "butterflies" in your stomach, heart pounding, startling easily, and muscle tension. This condition, which often remains undetected and untreated, undermines a person's ability to become self-sufficient and impedes efforts to reduce welfare costs through return-to-work programs. Patients with this disorder commonly underperform educationally; have a lower probability of marrying, a lower economic status, and a higher probability of losing their job. The early onset of symptoms in adolescence interferes with the acquisition of social skills, resulting in social isolation. Patients with anxiety disorders are frequent users of the public health system. All these problems can be worsened if the anxiety disorder is accompanied by other mental disorders. Nevertheless, anxiety disorder is commonly under-diagnosed. The limitation of lives and the economic and social problems are always underestimated. An early diagnosis and treatment are key elements for lowering the social and economic burden of social anxiety disorder. If left untreated, anxiety disorders can have severe consequences resulting in avoidance behavior which may create problems by conflicting with job requirements, family obligations or other basic activities of daily living. Moreover, many people who suffer from an untreated anxiety disorder are prone to other psychological disorders, such as depression, and they have a greater tendency to abuse alcohol and other drugs. Their relationships with family members, friends and coworkers may become very strained, while their job performance may falter.

As described above, Anxiety Disorders categorize a large number of disorders where the primary feature is abnormal or inappropriate anxiety. These symptoms can occur without any recognizable stimulus or when the stimulus does not warrant such a reaction and can interfere with day to day living. The present invention provides novel methods and compositions, dosage forms, packages, and kits for preventing or treating anxiety disorders. The method and composition of the invention is adapted to modulate, prevent, alleviate, ameliorate, reduce or treat the symptoms of anxiety disorders. In some embodiments, administration of the compositions and methods of the present invention may prevent an anxiety disorder including including Post Traumatic Stress Disorder (PTSD) from developing. In other embodiments, administration of the compositions and methods of the present invention may prevent recurrent episodes of an anxiety disorder.

Preferably the composition of the invention is used in a method for preventing or treating anxiety disorders, said anxiety disorders being selected among Post Traumatic Stress Disorder (PTSD), panic symptom, persistent worry, doubt, dread, fear, uneasiness, obsessive thoughts, repeated thoughts, flashbacks of traumatic experiences, mood instability, agitation, restlessness, dyspepsia, headaches, dyspnea, nightmares, ritualistic behaviors, insomnia, cold or sweaty hands and/or feet, shortness of breath, palpitations, hyper alertness, exaggerated startle response, avoidance of particular activities, avoidance of particular thoughts, diminished intensity of feelings, dry mouth, numbness or tingling in the hands or feet, nausea, muscle tension, or dizziness.

By the term "mood disorders", is intended, for the purpose of this invention, disturbances in emotions that inhibit an individual from functioning well be it depression or mania.

Preferably, the composition of the invention provides a method for improving or boosting mood comprises the enhancement of the vigour and the alleviation of mood disorders said mood disorders being preferably selected among depression and/or mania.

A "depressive disorder" or depression is an illness that involves the body, mood, and thoughts. It interferes with daily life, normal functioning, and causes pain for both the person with the disorder and those who care about him or her.

A depressive disorder is not the same as a passing blue mood. It is not a sign of personal weakness or a condition that can be willed or wished away. People with a depressive illness cannot merely "pull themselves together" and get better. Without treatment, symptoms can last for weeks, months, or years. Depression is a common but serious illness, and most people who experience it need treatment to get better. Depressive disorders come in different forms. There are variations in the number of symptoms as well as their severity and persistence.

The present composition of the invention takes regulation as foundation and relieves stressed mood, so that the spirit is free from worry and relaxed to achieve the effect of preventing, improving and treating dismal and depression effectively.

The present invention also provides a method for treating fatigue and/or mood disorders and/or improving satiety and/or vitality in a subject in need thereof.

In a further embodiment of the invention, the composition of the invention is used in a method for improving or boosting or raising energy (i.e. the energy level) of a subject. While insomnia can leave one feeling drained in the day, it certainly isn't the only cause. Colds, seasonal affective disorder, and stress all play their part, too. Lack of energy can be described as tiredness, weariness, lethargy or fatigue. It can be accompanied by depression, decreased motivation, or apathy. Lack of energy can be a normal response to inadequate sleep, overexertion, overworking, stress, lack of exercise, or boredom. When part of a normal response, lack of energy often resolves with rest, adequate sleep, stress management, and good nutrition. Persistent lack of energy that does not resolve with self-care may be an indication of an underlying physical or psychological disorder.

The composition of the invention is adapted for increasing or raising energy in a subject and it surprisingly shown a:
Decreased need for sleep with little fatigue
An increase in goal-directed activities
Restlessness "Tension" or "Stress" can be defined as the way you feel when you're under abnormal pressure. All sorts of situations can cause stress. The most common involve work, money matters and relationships with partners, children or other family members. Tensions or stress may be caused either by major upheavals and life events such as divorce, unemployment, moving house and bereavement, or by a series of minor irritations such as feeling undervalued at work or dealing with difficult children. Sometimes there are no obvious causes. Stressful events that are outside the range of normal human experience may lead to post-traumatic stress disorder (PTSD).

Some stress can be positive. Research shows that a moderate level of stress makes us perform better. It also makes us more alert and can help us perform better in situations such as job interviews or public speaking Stressful situations can also be exhilarating and some people actually thrive on the excitement that comes with dangerous sports or other high-risk activities. But stress is only healthy if it is short-lived. Excessive or prolonged stress can lead to illness and physical and emotional exhaustion.

Among the symptoms associated with stress due to a state of alarm include adrenaline production, muscular tension, short term resistance as a coping mechanism, exhaustion, degrees of acute and persistent fatigue, irritability, inability to concentrate, and physiological effects such as elevated heart rate and blood pressure. In an acute episode and definitely in the prolonged, chronic state of stress, bodily functions are often altered. Stress can affect the immune system, the neuroendocrine axis, reasoning ability, concentration and other measurable parameters of cognition, and cause cardiopulmonary instability. Common physically symptoms such as aches/pains, fatigue or a "lack of energy", gastrointestinal symptoms, a lack of appetite, lightheadedness, dizziness, tachycardia, chest discomfort, insomnia, and a prevalence of colds due to an altered immune system. Mental effects can include experiencing concentration and memory problems, poor judgment, anxiousness, a jittery sensation with a state of chronic worrying, each of which can result in a vicious cycle of increasing stress.

Preferably the composition of the invention is used in a method for reducing tensions or stress comprising the reduction of adrenaline production, muscular tension, short term resistance as a coping mechanism, exhaustion, degrees of acute and persistent fatigue, irritability, inability to concentrate, aches/pains, fatigue or a "lack of energy", the lack of appetite, lightheadedness, chest discomfort, insomnia, the prevalence of colds, poor judgment, chronic worrying, the lack of reasoning ability, the lack of concentration.

To maintain, restore and prevent further chronic stressful influence on mind and body, the composition of the invention is a perfect remedy to balance the body's nervous system. In this particular embodiment, the composition of the invention is adapted to relieve or reduce tension or stress and relax.

It is a further object to provide a method for preventing, treating, ameliorating or alleviating symptoms of an anxiety disorder, sleep disorders, fatigue, mood disorder, tensions or stress disorder and/or lack of energy in a human subject suffering from or at risk for said symptoms comprising administering to a human in need of such treatment the composition of the invention comprising ellagitannins rich extracts originated from plant extracts of the Fagaceae family containing Roburins or derivatives thereof, in an amount effective to prevent, ameliorate or alleviate one or more of said symptoms or disorders.

The composition has the advantages of simple preparation, stable process conditions, and suitability for large-scale industrial production.

Those plant extracts are also referred as "ellagitannins rich extracts".

The ellagitannins are a diverse class of hydrolyzable tannins, a type of polyphenol formed primarily from the oxidative linkage of galloyl groups in 1,2,3,4,6-Pentagalloyl glucose. Ellagitannins differ from gallotannins, in that their galloyl groups are linked through C-C bonds, whereas the galloyl groups in gallotannins are linked by depside bonds. Ellagitannins comprise (Roburins A, B, C, D, E, Vescalin, Castalin, Vescalagin, Castalagin).

Preferably said ellagitannins rich extracts originated from plant extracts of the Fagacaea family comprise Roburins or derivatives thereof. Roburins include Roburins A, B, C, D, E In the present invention the term "Roburins" will be considered as equivalent to Roburins A, B, C, D, E and are interchangeable.

Roburin A is a tannin found for example in oak wood (*Quercus robur* and *Quercus petraea* or *Quercus alba*) or oak cork (*Quercus suber*). It is a dimeric compound, composed of two vescalagin subunits probably linked through an ether bond between the diphenyl group of one subunit and the triphenoyl moiety of the other one.

Preferably the plant extracts of the Fagacaea family are selected among genera *Quercus*, *Castanea*, and *Fagus* or mixtures thereof. Among the Fagaceae, particularly worthy of mention are the *Fagus grandifolia*, common beech (*Fagus sylvatica*), sweet chestnut (*Castanea sativa*) and English oak (*Quercus robur*).

Most preferably, the plant extracts of the Fagacaea family consists of oak woods extracts.

Even more preferably, the plant extracts of the Fagacaea family consists of *Quercus robur* extracts.

"*Quercus robur*" also know as "oak wood" belongs to the family of Fagaceae and the genus *Quercus*. *Quercus robur* (sometimes considered *Q. pedunculata*) is commonly known as Pedunculate oak or English oak. Also included in this definition of "oak wood" is the white oak, *Quercus alba*, *Quercus brutia Tenore*, *Q. pedunculiflora*, *Q. haas* as well as the Sessile Oak (*Q. petraea*). In the present invention the term "Quercus robur" will be considered as equivalent to oak wood as defined above, they are interchangeable.

Gathering: felling of the trees under National Forest Office control, from October to April when the sap is down. Oak wood is traditionally used to make wine barrels and is known to give its taste to wine and to contribute to its antioxidant activity. Fresh wood chips used for Biolandes extract are purchased from a famous wine barrel maker (http://www.dargaud-jaegle.com/) and obtained from Oak trees rigorously selected.

The extraction process is carried out by water extraction at low temperature (50° C.) and spray drying. No petrochemical solvent is used.

Oak wood extract contains ellagitannins (Roburins A, B, C, D, E, Vescalin, Castalin, Vescalagin, Castalagin) and phenolic acids (gallic acid, ellagic acid).

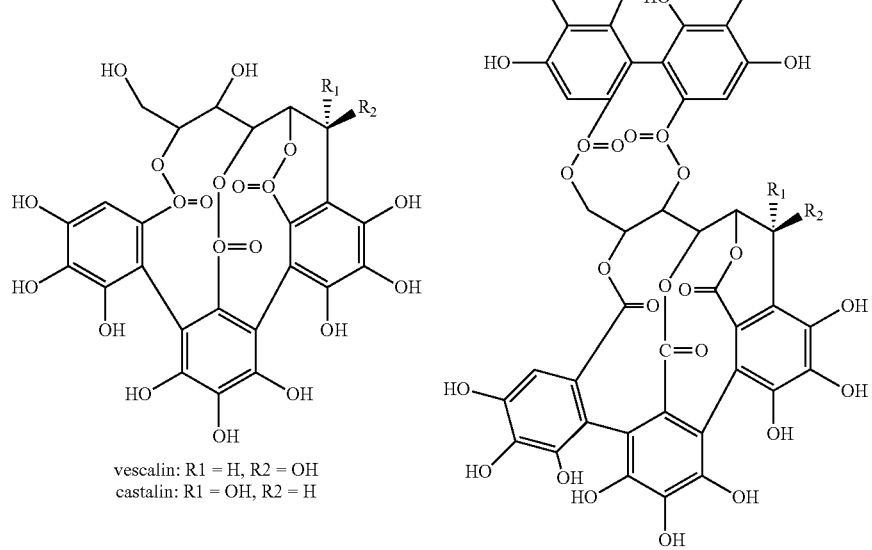

vescalin: R1 = H, R2 = OH
castalin: R1 = OH, R2 = H

V - vescalagin: R1 = H, R2 = OH
VII - castalagin: R1 = OH, R2 = H
VII - grandinin: R1 = H, R2 = Lyxose
VIII - roburin: E R1 = H, R2, Xylose

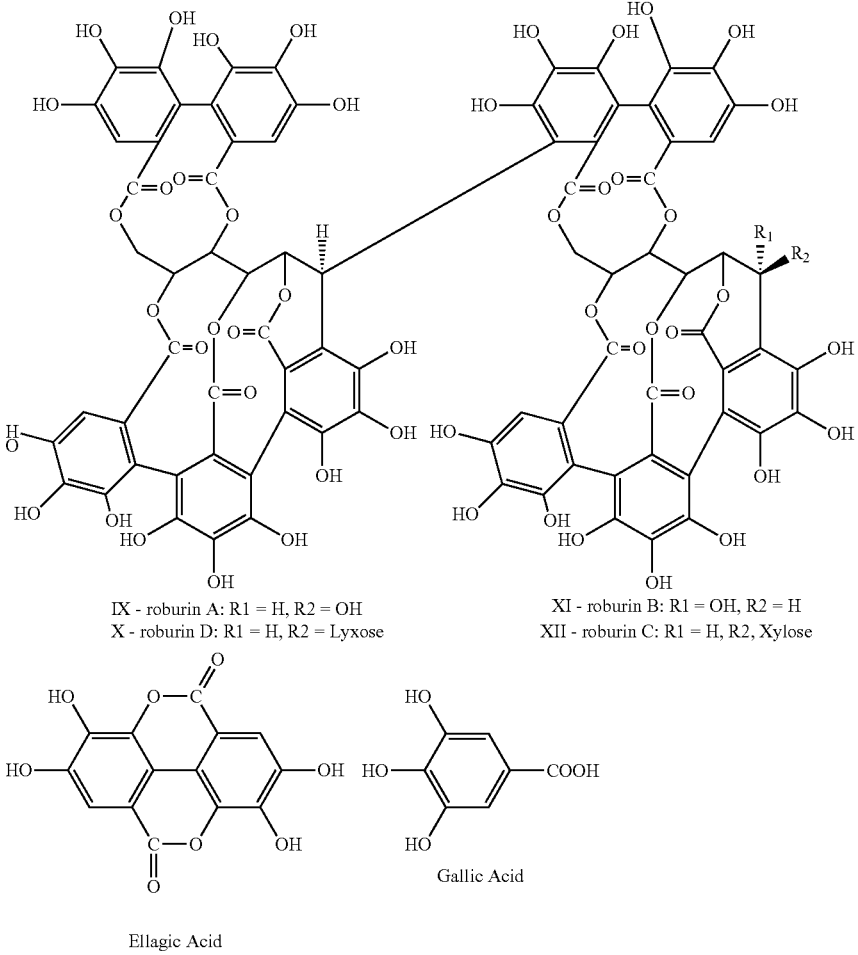

IX - roburin A: R1 = H, R2 = OH
X - roburin D: R1 = H, R2 = Lyxose

XI - roburin B: R1 = OH, R2 = H
XII - roburin C: R1 = H, R2, Xylose

Ellagic Acid

Gallic Acid

The composition consisting of ellagitannins, present in the preparation of the invention, is originated from a plant extract or alternatively from a synthesized material (i.e., synthetic ellagitannins, i.e. roburins).

Ellagitannins containing rich extracts are natural and preferably plant extracts having more than 50% by weight (of dried extracts) of ellagitannins (in particular roburins), more preferably more than 70% by weight and even more preferably more than 75% by weight of ellagitannins (in particular roburins). Preferably the plant extract according to the present invention is originated from oak wood extracts and more preferably the plant extract is *Quercus robur*.

In a preferred embodiment, the composition may contain ellagitannins (in particular roburins) at a concentration of 10% to 100% of total weight. For example, the composition of the invention may be diluted or concentrated to contain 10%, 20%, 30%, 40%, 50%, 60%, 70%, 75%, 80%, 90% or 95% ellagitannins (in particular roburins). Concentration may be performed using known methods such as column chromatography or affinity chromatography.

The composition of the invention may further comprise vitamins, coenzymes, mineral substances, aminoacids and antioxidants and/or a suitable excipient q.s.p. The composition may be manufactured in the form of tablets, lozenges, capsules, pills, granulates, syrups, vials or drops.

The suitable excipient of the invention is an acceptable excipient or carrier as defined above.

Examples of suitable excipients of this invention include, but are not limited to, anti-adherents, binders (e.g., macrocrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof.

For example, the composition of the present invention may further include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

Optionally the composition of the present invention may include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and combinations thereof.

In a preferred embodiment of the invention, the suitable excipient is a pharmaceutically acceptable excipient.

The present invention further provides for a food preparation, a dietary or food supplement, a nutraceutical, a beverage, a medicament and a topical preparation comprising the composition of the present invention. According to a preferred embodiment of the composition of the invention is a beverage consisting in an energy drink.

Preferably, the dietary supplement, the nutraceutical or the medicament of the present invention is administered at a dosage of between 5 mg per day to 2,000 mg per day. Preferably between 50 mg to 1,000 mg per day and even more preferably between 100 mg to 400 mg per day.

The preparation, the dietary supplement, the nutraceutical or the medicament of the present invention can be administered orally, parenterally or topically at a dosage of between 5 mg per day to 2,000 mg per day. Preferably between 50 mg to 1,000 mg per day and more preferably between 100 mg to 400 mg per day.

If intended for oral administration, the medicament of the present invention can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a solution for intravenous, intramuscular or subcutaneous injection.

The topical preparations according to the present invention can be, but not limited to, a cream, a patch, a gel, an ointment, a lotion, a tincture, a spray, a mousse, a cleansing composition or a foam. The topical preparations of the present invention can be also in the form of a suspension or dispersion in solvents or fatty substances, or alternatively in the form of an emulsion or micro emulsion, PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

The composition of the invention being in therapeutically effective amounts so that, when the composition is administered at least daily over a period of time, in a sufficient amount, it prevents or treats fatigue, anxiety and sleep disorders, improves mood, reduces tension and raises energy in a subject by an end of the period of time.

The administering includes initially administering an elevated dosage of the composition of the invention to attain the enhanced level of energy by the end of the period of time and thereafter administering a dosage of the composition daily that contains less of the composition than the elevated dosage and still provide the enhanced level of energy.

The composition of the invention may be used in a food preparation, a dietary supplement, a medicament, a nutraceutical, or a beverage.

Preferably, the composition or the medicament of the invention is administered orally, parenterally or topically as defined above.

An oral administration of the blend in accordance with an administration regimen over a prolonged period of time provides certain benefits, which include: helping to reduce fatigue, anxiety and sleep disorders, protecting, restoring, improving and/or sustaining good mood, reducing tensions or stress and raising or boosting energy in a subject.

The blend or composition of the present invention may be in the form of a composition, taken either in tablet form or in liquid form. Alternatively, the blend may be in the form of the ingredients being in separate, distinct tablet or liquid form but packaged together in a kit. In the latter case, the separate ingredients are taken either simultaneously, such as by mixing them together if in liquid form, or one after another if in tablet form.

In one embodiment of the invention, the composition or the medicament of the invention is administered at a dosage of between 5 mg per day to 2,000 mg per day. The subject in need thereof is a mammal, preferably a human.

A unit dosage comprises a therapeutically effective daily amount of the composition of the invention which may be taken as a single daily administration or by multiple small doses taken over the course of a day.

Also encompassed is a kit comprising the composition of the invention.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practicing the present invention and are not intended to limit the scope of the invention.

EXAMPLES

Example 1

The aim of the study was to investigate some biological activities of *Quercus Robur* extract (further QR) in human – effect on symptoms of fatigue, some biochemical parameters and parameters of glycooxidative and oxidative stresses as well as inflammation markers.

The study was approved by Etical Commettee on January 10$^{th}$ 2011.

Exclusion criteria for volunteers included into the study were:
- acute inflammatory diseases
- renal and cardiovascular disorders
- diabetes mellitus
- women with HRT (hormone replacement therapy)
- requirement of medication prescription Volunteers were not supplemented with vitamins E and C as well as some other antioxidants during the study.

1.1. VOLUNTEERS 20 healthy volunteers of age 45-65 (8 males and 12 females) were included in this study. The ethical committee of the Medical School, Bratislava, Slovak Republic has approved the study, and all participants have signed the written informed consent.
Before including in the study – volunteers were educated about the diet – normal diet with exclusion of additional antioxidants and for the period of two weeks volunteers only have respected this type of diet (run-in period). This diet had to be respected till the end of project.

During the next 4 weeks (intervention period) volunteers were administered 3 times daily with 1 capsule of 100 mg of QR extract. This period was followed by 2 weeks of wash-out period without QR administration.

At the beginning of the study, individual data of volunteers were taken: sex, age, education level, smoking/non-smoking status, at female – menopause status, blood pressure, waist circumference, BMI (Body mass Index).

Volunteers were investigated before intervention period (0-sampling), immediately after intervention period (4-sampling) and 2 weeks after termination of QR administration - wash-out period (6-sampling).

Symptoms of fatigue and mood were investigated by AD ACL questionnaire (The Activation-Deactivation Adjective Check List) (Thayer 1967). This questionnaire was filled out by volunteers at home every week (on Friday evening)) between the 0-sampling and 6-sampling (e.g. seven times – questionnaires (Q) 0,1,2,3,4,5,6)

In all samplings (0,4,6) volunteers were investigated in the presence of medical doctor and in cooperation with nurse as follows:
1. The basic clinical investigation (weight, blood pressure, possible side-effects)
2. The blood (for serum and plasma) as well as urine samples were taken for determination of individual biochemical parameters according to the protocol. (Tables 1&2)

2. METHODS

2.1. AD ACL (ACTIVATION-DEACTIVATION ADJECTIVE CHECK LIST) QUESTIONNAIRE (Thayer, R. E. :The biopsychology of mood and arousal. New York: Oxford University Press. 1989)

The AD ACL is a multidimensional test of various transitory arousal states, including energetic and tense arousal. AD ACL Short Form consists of 20 self-descriptive adjectives of Energy (A1 subscale), Tiredness (A2 subscale), Tension (B1 subscale), and Calmness (B2 subscale). The AD ACL is scored by assigning 4, 3, 2, and 1, respectively to the "vv, v, ?" and "no" scale points, and summing or averaging the five scores for each subscale. In order of appearance, the subscale adjectives are as follows: Energetic A1 (active, energetic, vigorous, lively, full-of-pep); Tired A2 (sleepy, tired, drowsy, wide-awake, wakeful); Tension B1 (jittery, intense, fearful, clutched-up, tense); B2 Calmness (placid, calm, at-rest, still, quiet). Scoring for "wakeful" and "wide-awake" must be reversed for the Tiredness subscale. Tiredness and Tension scores must be reversed (but not wakeful and wide-awake in this case) before summing the ten scores.

Scoring is based on four possible points for each adjective thus the possible score was in range 0-80 (each of subscales 1-20). Volunteers were instructed to rate each adjective in the context of how they felt at the moment they were making their responses. Participants were instructed to fill out the questionnaire on Friday evening.

*Volunteer No.:*            *Questionnaire No.:*

Questionnaire AD-ACL

Each of the words on the back describes feelings or mood. Please use the rating scale next to each word to describe your feelings at this moment.

EXAMPLES

| relaxed | ✓✓ | ✓ | ? | no | If you circle the double check (✓✓) it means that you *definitely* feel relaxed *at the moment*. |
|---|---|---|---|---|---|
| relaxed | ✓✓ | ✓ | ? | no | If you circle the single check (✓) it means that you feel slightly relaxed *at the moment*. |
| relaxed | ✓✓ | ✓ | ? | no | If you circled the question mark (?) it means that the word does not apply or you cannot decide if you feel relaxed *at the moment*. |
| relaxed | ✓✓ | ✓ | ? | no | If you circled the no it means that you are *definitely not relaxed at the moment*. |

Work rapidly, but please mark all the words. Your first reaction is best. This should take only a minute or two.

Table 1

*Volunteer No.:*                                                *Questionnaire No.:*

(Back page)

| ✓✓ | ✓ | ? | no | definitely feel |
|---|---|---|---|---|
| ✓✓ | ✓ | ? | no | feel slightly |
| ✓✓ | ✓ | ? | no | cannot decide |
| ✓✓ | ✓ | ? | no | definitely do not feel |

(First row: ✓✓ circled; Second row: ✓ circled; Third row: ? circled; Fourth row: no circled)

| | | | | |
|---|---|---|---|---|
| active | ✓✓ | ✓ | ? | no |
| placid | ✓✓ | ✓ | ? | no |
| sleepy | ✓✓ | ✓ | ? | no |
| jittery | ✓✓ | ✓ | ? | no |
| energetic | ✓✓ | ✓ | ? | no |
| intense | ✓✓ | ✓ | ? | no |
| calm | ✓✓ | ✓ | ? | no |
| tired | ✓✓ | ✓ | ? | no |
| vigorous | ✓✓ | ✓ | ? | no |
| at-rest | ✓✓ | ✓ | ? | no |
| drowsy | ✓✓ | ✓ | ? | no |
| fearful | ✓✓ | ✓ | ? | no |
| lively | ✓✓ | ✓ | ? | no |
| still | ✓✓ | ✓ | ? | no |
| wide-awake | ✓✓ | ✓ | ? | no |
| clutched-up | ✓✓ | ✓ | ? | no |
| quiet | ✓✓ | ✓ | ? | no |
| full-of-pep | ✓✓ | ✓ | ? | no |
| tense | ✓✓ | ✓ | ? | no |
| wakeful | ✓✓ | ✓ | ? | no |

Table 2

Statistical analysis of biochemical and oxidative stress parameters

Analyses were carried out using statistical tools of Microsoft Office Excel 2003. For comparison of results in different samplings for normally distributed data we have used paired Student t-test. Significance at level of 0.05 was used to determine statistical significance.

3. RESULTS

All 20 volunteers enrolled in the project have finished this study with all three samplings (0,4,6) and 19 volunteers have accomplished also all questionnaires.

Some values of score are missing as the questionnaires from 1 volunteer did not return because of personal problems.

None of volunteers dropped out the study for serious reasons.

The transcription of all values from an original output into tables were checked two times.

QUESTONNAIRES

20 healthy volunteers – 12 females (F) and 8 males (M) were enrolled in the project (average age 54,2 years).

Comparative analysis of average counts across response categories

In the comparative analysis of average counts across response categories (subscales) in Q1 (questionnaire No.1. – before QR administration) and Q5 (questionnaire No.5 – after 4 weeks of QR administration) we have found that scorings of subscales (blocks) are significantly differing from each other (p = 0.0022). Further, except the subscale B2 (calmness) the average score was increased in each subscale.

Average score in subscales at baseline and 4 week QR

|  | Baseline mean | 4 Weeks of QR mean |
|---|---|---|
| Subscale:A1 Energy | 2,4 | 2,610526 |
| Subscale:B2 Calmness | 2,463158 | 2,473684 |
| Subscale:A2 Tiredness | 2,715789 | 3,042105 |
| Subscale:B1 Tension | 3,663158 | 3,821053 |

Average increase of scores in the percentage of maximal score:

| 4 = 100% | % of maximal score | |
|---|---|---|
|  | Baseline | 4 Weeks of QR |
| Subscale:A1 Energy | 60.0000 | 65.2632 |
| Subscale:B2 Calmness | 61.5790 | 61.8421 |
| Subscale:A2 Tiredness | 67.8947 | 76.0526 |
| Subscale:B1 Tension | 91.5790 | 95.5263 |

Tables 3&4

SUBSCALE A1 Energy:

Paired t test

Differences between Energy score at baseline and Energy score at 4 weeks:

Mean of differences = -0,2105 (n = 95)

Standard deviation = 0,8492

Standard error = 0,0871

95% CI = -0,3835 to -0,0375 df = 94 t = -2,4163

One sided P = 0,0088

Two sided P = 0,0176

After treatment, the volunteers have significantly increased score for energy (i.e. for each of A1 questions Energy) by 0.21 points on average).

Conclusion: 4 weeks of QR administration significantly improved the energy score. The subjects felt more energetic. The improvement is statistically significant.

SUBSCALE B2 Calmness:

Paired t test

Differences between calmness (B2) score at baseline and calmness (B2) score at 4 weeks:
Mean of differences = -0,0105 (n = 95),
Standard deviation = 0,9396
Standard error = 0,0964
95% CI = -0,2019 to 0,1809
df = 94
t = -0,1092
One sided P = 0,4566
Two sided P = 0,9133 – non significant

SUBSCALE A2: Tiredness

Paired t test
Differences between tiredness (A2) score at baseline and tiredness (A2) score at 4 weeks:
Mean of differences = -0,3263 (n = 95)
Standard deviation = 1,1526
Standard error = 0,1183
95% CI = -0,5611 to -0,0915
df = 94
t = -2,7594
One sided P = 0,0035
Two sided P = 0,007 (after treatment, the volunteers have significantly improved their score for tiredness (i.e. for each of A2 questions: Tiredness) by 0.3261 points on average).

Conclusion: 4 weeks of QR administration significantly improved the fatigue score. The subjects felt less tired. The improvement is statistically significant.

SUBSCALE B1: Tension

Paired t test
Differences of the tension (B1) scores between baseline and 4 weeks of QR:
Mean of differences = -0,1579 (n = 95)
Standard deviation = 0,6411
Standard error = 0,0658
95% CI = -0,2885 to -0,0273
df = 94
t = -2,4006
One sided P = 0,0092
Two sided P = 0,0183 (after treatment, the volunteers have significantly improved their score for tension (i.e. for each of B1 questions: Tension) by 0.158 points on average).

Conclusion: 4 weeks of QR administration significantly improved the tension score. The subjects felt less tense. The improvement is statistically significant.

Comparison of total scores reached in the questionnaires using stratification of data according to the level of summarized baseline points Participants were stratified into two groups, those with a summary subscale score below 14 points and those who achieved 14 and more points at baseline. For the total score, a 60 point result was chosen as a cut-off-point (20-59 the 1$^{st}$ subgroup and 60-80 was the 2$^{nd}$ one).

COMPARISON OF TOTAL SCORES (20-80 points) REACHED IN THE QUESTIONNAIRES

In the second group (baseline higher than 60 points) no effect was found.

As expected, in the first group (baseline lower than 60 points) after 4 weeks QR total score was significantly increased by 6.7 points on average in comparison with baseline P (0.0371).

Paired t test
For differences between 1 total and 5 total:
Mean of differences = -6,7 (n = 10)
Standard deviation = 10,4886
Standard error = 3,3168
95% CI = -14,2031 to 0,8031
df = 9
t = -2,02
One sided P = 0,0371
Two sided P = 0,0741

The overall scores of the AD ACL questionnaire was significantly increased in subjects with a baseline score lower than 60 points.

Summarizing results in AD ACL questionnaire:

This analysis was focused on the comparison of pre-post treatment effect of QR extract on symptoms of fatigue and mood. Those symptoms were represented by the feeling adjectives in the questionnaire AD ACL. Volunteers could give the score 1-4 points for each of 20 adjectives describing different feelings and total score 20-80 points in the questionnaire as well as total score 5-20 in each of 4 subscales (with 5 feelings).

<u>Average score for the question</u> (feeling) was significantly increased in 3 from 4 subscales:

- Subscale A1 (Energy) average score was increased by 0.21 points ($p = 0.0176$),
- subscale A2 (Tiredness) by 0.326 points ($p = 0.007$) and
- subscale B1 (Tension) by 0.178 points ($p = 0.0183$).

Conclusion: QR administration for 4 weeks significantly improved the scores of energy, fatigue (tiredness) and tension in healthy volunteers.

Example 2

The present study evaluated 41 subjects characterized as having Chronic Fatigue Syndrome and an increased oxidative stress (PFR) without any other clinical or metabolic condition.

The subjects received 3 QR capsules/day were used for 4 weeks.

The multidimensional assessment of fatigue scale was used to assess fatigue before and after treatment.

Measurements of Plasma free radicals A FRAS 4 (Free Radicals Analitycal System; H&D, Parma, It) system was used. The test is used to detect oxidative stress (D-Roms test) in plasma and has been used and validated in several studies involving both normal subjects and patients and the validation of different types of treatment. The equipment has been used widely, particularly in our population.

MULTIDIMENSIONAL ASSESSMENT OF FATIGUE (MAF) SCALE

Instructions: These questions are about fatigue and the effect of fatigue on your activities.

For each of the following questions, circle the number that most closely indicates how you have been feeling during the past week.

For example, suppose you really like to sleep late in the mornings. You would probably circle the number closer to the "a great deal" end of the line. This is where I put it:

Example: To what degree do you usually like to sleep late in the mornings?

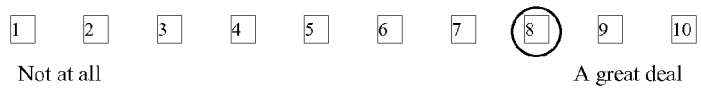

Now please complete the following items based on the past week.

1. To what degree have you experienced fatigue?

| If no fatigue, stop here. |

2. How severe is the fatigue which you have been experiencing?

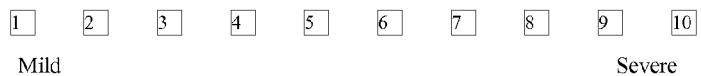

3. To what degree has fatigue caused you distress?

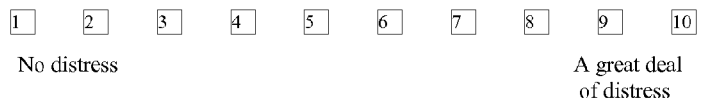

MULTIDIMENSIONAL ASSESSMENT OF FATIGUE (MAF) SCALE (Continued)

Circle the number that most closely indicates to what degree fatigue has interfered with your ability to do the following activities in the past week. For activities you don't do, for reasons other than fatigue (e.g. you don't work because you are retired), check the box.

In the past week, to what degree has fatigue interfered with your ability to:

(NOTE: Check box to the left of each number if you don't do activity)

☐ 4. Do household chores

| 1 | 2 | 3 | 4 | 5 | 6 | 7 | 8 | 9 | 10 |

Not at all                          A great deal

☐ 5. Cook

| 1 | 2 | 3 | 4 | 5 | 6 | 7 | 8 | 9 | 10 |

Not at all                          A great deal

☐ 6. Bathe or wash

| 1 | 2 | 3 | 4 | 5 | 6 | 7 | 8 | 9 | 10 |

Not at all                          A great deal

☐ 7. Dress

| 1 | 2 | 3 | 4 | 5 | 6 | 7 | 8 | 9 | 10 |

Not at all                          A great deal

☐ 8. Work

| 1 | 2 | 3 | 4 | 5 | 6 | 7 | 8 | 9 | 10 |

Not at all                          A great deal

☐ 9. Visit or socialize with friends or family

| 1 | 2 | 3 | 4 | 5 | 6 | 7 | 8 | 9 | 10 |

Not at all                          A great deal

MULTIDIMENSIONAL ASSESSMENT OF FATIGUE (MAF) SCALE (Continued)
(NOTE: Check box to the left of each number if you don't do activity)

☐ 10. Engage in sexual activity

| 1 | 2 | 3 | 4 | 5 | 6 | 7 | 8 | 9 | 10 |

Not at all                                            A great deal

☐ 11. Engage in leisure and recreational activities

| 1 | 2 | 3 | 4 | 5 | 6 | 7 | 8 | 9 | 10 |

Not at all                                            A great deal

☐ 12. Shop and do errands

| 1 | 2 | 3 | 4 | 5 | 6 | 7 | 8 | 9 | 10 |

Not at all                                            A great deal

☐ 13. Walk

| 1 | 2 | 3 | 4 | 5 | 6 | 7 | 8 | 9 | 10 |

Not at all                                            A great deal

☐ 14. Exercise, other than walking

| 1 | 2 | 3 | 4 | 5 | 6 | 7 | 8 | 9 | 10 |

Not at all                                            A great deal

15. Over the past week, how often have you been fatigued?

- [4] Every day
- [3] Most, but not all days
- [2] Occasionally, but not most days
- [1] Hardly any days

16. To what degree has your fatigue changed during the past week?

- [4] Increased
- [3] Fatigue has gone up and down
- [2] Stayed the same
- [1] Decreased

Results:

Table 5 shows the Multidimensional Assessment of Fatigue (MAF) scale. In this part of the study 3 QR capsules/day were used for 4 weeks. This group includes 41 subjects (23 females; mean age 44.43;3.2) and in 38 comparable controls (22 females 44.32;6.3) . Subjects were characterized as having CFS and an increased oxidative stress (PFR) without any other clinical or metabolic condition.

| MAF QUESTIONS | | SCORE | |
|---|---|---|---|
| 1-14 | Controls | bef 7.11;2.2 | aft 7.09;2.1  ns |
|  | *QR* | *bef 7.32;1.9* | *aft 5.21;1.1\** |
| 15,16 | Controls | bef 3.32;1.40 | aft 3.41;1.1ns |
|  | *QR* | *bef 3.2;0.9* | *aft 2.1;0.7\** |
| MAF TOTAL | Controls | bef 10.43;1.8 | aft 10.5.;1.4ns |
|  | QR | bef 10.52;1.4 | aft 7.3;0.9\* |
| PFR | Controls | bef 464.33;49.32 | aft 455.6;42.5ns |
|  | QR | bef 459.6;55.1 | aft 339.31;41.5\* | p<0.05, Mann-Whitney, U-test (+ Anova)

ns: non significant, bef: before, aft: after

Table 5

Table 5: Multidimensional assessment of fatigue (MAF) scale. Results with 4 weeks of QR in patients with Chronique Fatigue Syndrome and increased oxidative stress (PFR).

Conclusion:

Results in table 5 indicate a significant improvement of fatigue (reduction in MAF score) and in the oxidative stress status as shown by Plasma Free Radical (PFR) values before and after treatment with QR. (3 cps/day) indicate a parallel improvement (with reduction in MAF score) and in PFR values.

Example 3

Effects of QR on chronic fatigue syndrome and mood

CHRONIC FATIGUE AND IMMUNE DYSFUNCTION SYNDROME (or CFIDS) General Health Status How many people have CFS? Estimates vary, but at least one million Americans have CFS and millions more suffer worldwide. Several studies have been conducted in the U.S. and other countries, but the difficulty in pinpointing a number arises from the different definitions and case criteria used over time and between research groups. More than 80% of people identified in community studies of CFS have not been diagnosed and are not receiving appropriate medical care for their illness.

CFS does not discriminate. It strikes people of all age, racial, ethnic and socioeconomic groups. Research has shown that it is 3-4 times more common in women compared to men, a rate similar to that of autoimmune conditions like multiple sclerosis and lupus. Teens are more likely to get CFS than younger children, and adults are more likely to get CFS than teens.

Researchers at DePaul University estimate that every year CFS costs the U.S. economy $17-24 billion. Its prevalence, economic effect, disabling impact and chronicity make it one of the most burdensome conditions of our time.

CFS QUESTIONNAIRE

1. Have you felt generally "unwell" for three months or longer?
Yes
No

2. Activity Tolerance

Can you still do most or all of the physical and mental activities you did before you began feeling unwell?

Yes
No

3. Impact on Activity Level
Has your illness had a major impact on work, social, and/or educational activities, to the extent that you have had to make adjustments in your lifestyle in an effort to avoid relapsing or becoming more ill?

Yes
No

Symptoms
Do you have at least four (4) of the following eight (8) symptoms?

- 1. Weakness and exhaustion, lasting more than 24 hours, following mental or physical activity
- 2. Unrefreshing sleep
- 3. Substantial impairment of short-term memory or concentration
- 4. Muscle pain
- 5. Pain in the joints, without swelling or redness
- 6. Headaches of a new type, pattern or severity
- 7. Tender armpit and/or neck lymph nodes
- 8. Sore throat Yes
NO The definition for CFS requires that a person have 4 (four) of these 8 (eight) symptoms in addition to six months or more of unrelenting fatigue. However, the definition is designed for research purposes. In treating individual patients, many health care providers apply the guidelines less rigidly.

Please continue with the next question if you have three (3) of these symptoms. If you have only one or two, it's unlikely that you have CFS.

Other Common Symptoms
Do you have at least four (4) of these symptoms that are common in persons with CFS, but are not part of the research definition?

- 9. Sensitivity to noise, foods, medications, and chemicals
- 10. Gastro-intestinal symptoms such as abdominal pain, diarrhea, irritable bowel
- 11. Periodic or persistent dizziness or lightheadedness
- 12. Depression
- 13. Mood swings

- 14. Weight changes without changes in diet or activity level
- 15. Alcohol intolerance
- 16. Increased allergies
- 18. Visual disturbances such as blurring, sensitivity to light, eye pain, frequent prescription changes Yes
No Next Steps
If you have fewer than four (4) of the case definition symptoms and fewer than four (4) of other common symptoms, it's unlikely that you have CFS.
You may wish to learn more about conditions that share some symptoms with CFS to see if these are more likely diagnoses for your particular case.

Methods:

24 PATIENTS with chronic fatigue syndrome;
26 CONTROLS;
AGE RANGE 40-55
NO OTHER CLINICAL PROBLEMS OR DRUG
Blood tests: normal at inclusion
TREATMENT: QR 300 mg
INCLUSION: after 6 months of stable problems indicating CFS

Methods:

The CFS QUESTIONNAIRE

1. Have you felt generally "unwell" for three months or longer?

◯ Yes
   ◯ No

2. Activity Tolerance
   Can you still do most or all of the physical and mental activities you did before you began feeling unwell?

◯ Yes
   ◯ No

3. Impact on Activity Level
   Has your illness had a major impact on work, social, and/or educational activities, to the extent that you have had to make adjustments in your lifestyle in an effort to avoid relapsing or becoming more ill?

◯ Yes
   ◯ No

Symptoms
Do you have at least four (4) of the following eight (8) symptoms?
- 1. Weakness and exhaustion, lasting more than 24 hours, following mental or physical activity
- 2. Unrefreshing sleep
- 3. Substantial impairment of short-term memory or concentration
- 4. Muscle pain
- 5. Pain in the joints, without swelling or redness
- 6. Headaches of a new type, pattern or severity
- 7. Tender armpit and/or neck lymph nodes
- 8. Sore throat ◯ Yes
◯ No Symptoms The strict case definition for CFS requires that a person have 4 (four) of these 8 (eight) symptoms in addition to six months or more of unrelenting fatigue. However, the definition is designed for research purposes. In treating individual patients, many health care providers apply the guidelines less rigidly.

Please continue with the next question if you have three (3) of these symptoms. If you have only one or two, it's unlikely that you have CFS.

Other Common Symptoms
Do you have at least four (4) of these symptoms that are common in persons with CFS, but are not part of the research definition?
- 9. Sensitivity to noise, foods, medications, and chemicals
- 10. Gastro-intestinal symptoms such as abdominal pain, diarrhea, irritable bowel
- 11. Periodic or persistent dizziness or lightheadedness
- 12. Depression
- 13. Mood swings
- 14. Weight changes without changes in diet or activity level
- 15. Alcohol intolerance
- 16. Increased allergies
- 18. Visual disturbances such as blurring, sensitivity to light, eye pain, frequent prescription changes ◯ Yes
◯ No Next Steps
If you have fewer than four (4) of the case definition symptoms and fewer than four (4) of other common symptoms, it's unlikely that you have CFS. You may wish to learn more about conditions that share some symptoms with CFS to see if these are more likely diagnoses for your particular case.

Brief Mood Introspection Scale (BMIS)
by John D. Mayer

INSTRUCTIONS: Circle the response on the scale below that indicates how well each adjective or phrase describes your present mood.

(definitely do not feel) (do not feel) (slightly feel) (definitely feel)

XX           X        V       VV

| | | | |
|---|---|---|---|
| Lively | XX X V VV | Drowsy | XX X V VV |
| Happy | XX X V VV | Grouchy | XX X V VV |
| Sad | XX X V VV | Peppy | XX X V VV |
| Tired | XX X V VV | Nervous | XX X V VV |
| Caring | XX X V VV | Calm | XX X V VV |
| Content | XX X V VV | Loving | XX X V VV |
| Gloomy | XX X V VV | Fed up | XX X V VV |
| Jittery | XX X V VV | Active | XX X V VV |

Overall, my mood is:

Very Unpleasant                         Very Pleasant

-10 -9 -8 -7 -6 -5 -4 -3 -2 -1 0 1 2 3 4 5 6 7 8 9 10

*Please Note: The "Overall, my mood is" section is usually omitted, although some people use it and fold it into the overall score.*

---

Original Citation: Mayer, J. D., & Gaschke, Y. N. (1988). The experience and meta-experience of mood. Journal of Personality and Social Psychology, 55, 102-111. [Scoring instructions are described there]

Some Other Articles that Have Used the Scale:

* Examination of the paths between personality, current mood, its evaluation, and emotion regulation. Kokkonen, Marja; Pulkkinen, Lea; European Journal of Personality, Vol 15(2), Mar-Apr 2001. pp. 83-104.
* Resolution of lexical ambiguity by emotional state. Halberstadt, Jamin B.; Niedenthal, Paula M.; Kushner, Julia; Psychological Science, Vol 6(5), Sep 1995. pp. 278-282.
* Intrusive thoughts as determinants of distress in parents of children with cancer. Hall, Martica; Baum, Andrew; Journal of Applied Social Psychology, Vol 25(14), Jul 1995. Special issue: Rumination and intrusive thoughts. pp. 1215-1230.
* Mood inductions for four specific moods: A procedure employing guided imagery vignettes with music. Mayer, John D.; Allen, Joshua P.; Beauregard, Keith; Journal of Mental Imagery, Vol 19(1-2), Spr-Sum 1995. pp. 151-159.
* Mood-congruent judgment over time. Mayer, John D.; Hanson, Ellen; Personality & Social Psychology Bulletin, Vol 21(3), Mar 1995. pp. 237-244.

*The scale has been used in many other articles; I do not have a comprehensive list at this time. If you know of other uses, I would be delighted to hear of them.

Results

Plasma free radicals:

| CARR UNITS DATA: | | inclusion | 3 months |
|---|---|---|---|
| | QR | 483;33 | 358;36 * |
| | CONTROLS | 469;31 | 476;43 |

CONTROLS DO NOT CHANGE AND MOSTLY WORSEN (WITH A HIGHER SCORE AT 3 MONTHS).

The CFS QUESTIONNAIRE RESULTS TABLE:

| MAIN SYMPTOMS | NORMALIZED SCORE 1-10 | | INCLUSION | 3 MONTHS |
|---|---|---|---|---|
| *= P<0.05 | | | | |
| 1. Weakness and exhaustion >24 hours | QR | | 7.7;1.2 | 6.7;0.9* |
| following mental or physical activity | | CONTR | 7.6;1 | 7.5;1.3 |
| 2. Unrefreshing sleep | | | 7.5;2.1 | 5.4;1* |
| | | | 7.6;1.1 | 7.5;1.3 |
| 3. Impairment of short-term memory | | | 7.8;2 | 7.1;1.1* |
| or concentration | | | 7.6;1.8 | 7.5;2.1 |
| 4. Muscle pain | | | 8.3;1.1 | 4.4;3.1* |
| | | | 8.1;1.4 | 7.9;1.1 |
| 5. Joints pain, no swelling/redness | | | 7.9;1.3 | 7.6;1.3* |
| | | | 7.6;1.5 | 7.6;1.4 |
| 6. Headaches | | | 7.6;2.3 | 6.9;1.1* |
| | | | 7.5;3.1 | 7.4;1.1 |
| 7. Tender armpit, neck lymph nodes | | | 4.7;1.3 | 3.2;1.2* |
| | | | 4.9;1.3 | 4.4;1.4 |
| 8. Sore throat | | | 5.3;3.1 | 4.9;3.2* |
| | | | 4.7;1.4 | 5.7;1.1 |

ACCESSORY Common Symptoms

| | | | | |
|---|---|---|---|---|
| 9. Sensitivity to noise, foods, medications, | | | 8.6;2.2 | 7.6;2.1* |
| chemicals | | | 8.3;1.2 | 7.9;0.9 |
| 10. Gastro-intestinal symptoms | | | 7.3;1.3 | 6.8;2* |
| abdominal pain, diarrhea, irritable bowel | | | 7.6;2.1 | 7.7;1.3 |
| 11. Periodic or persistent dizziness or | | | 6.9;2.4 | 5.4;2.2* |
| lightheadedness | | | 7.2;1 | 7.6;1-4 |
| 12. Depression | | | 7.4;1.9 | 7.3;3.2 |
| | | | 7.6;1.3 | 7.6;1.2 |
| 13. Mood swings | | | 8.2;1 | 7.5;2.1* |
| | | | 7.8;1.3 | 7.4;1.3 |

| | | |
|---|---|---|
| 14. Weight changes without changes in diet or activity level | 7.5;0.9<br>7.4;1.2 | 6.1;2.1*<br>7.5;1.8 |
| 15. Alcohol intolerance | 5.4;1.2<br>5.3;1.4 | 5.3;2.4<br>6.2;1.1 |
| 16. Increased allergies | 4.6;2.1<br>4.3;1.7 | 3.2;1.1*<br>5.3;1.6 |
| 18. Visual disturbances (blurring, sensitivity to light, eye pain, frequent prescription changes) | 7.5;1.1<br>7.3;1.3 | 7;1.1*<br>7.3;1.2 |

Table 6

Results MOOD with the BMIS

Brief Mood Introspection Scale (BMIS) in subjects with CFS: QR results

| BMIS POSITIVE ITEMS | | INCLUSION | END STUDY | P<br>* = P<0.05 |
|---|---|---|---|---|
| Active | QR SUBJECTS | 2;1.1 | 3.6;0.4 | * |
| | Controls | 2.3;0.8 | 2.2;0.4 | ns |
| Lively | | 1.1;0.3 | 2.4;0.5 | * |
| | | 2.1;0.3 | 2.05;0.6 | ns |
| Happy | | 1.2;0.5 | 3;0.5 | * |
| | | 1.4;0.6 | 1.4;0.4 | ns |
| Peppy | | 1.2;0.5 | 2.7;0.4 | * |
| | | 1.1;0.4 | 1.3;0.5 | ns |
| Caring | | 1.4;0.5 | 2.9;0.4 | * |
| | | 1.5;0.6 | 1.2;0.5 | ns |
| Calm | | 1;0.5 | 2.8;0.5 | * |
| | | 1.2;0.6 | 1.2;0.3 | ns |
| Content | | 1.4;0.6 | 2.9;0.4 | * |
| | | 1.3;0.5 | 1.4;0.4 | ns |
| Loving | | 1.3;0.4 | 2.9;0.4 | * |
| | | 1.2;0.6 | 1.3;0.7 | ns |
| total QR | | 10.6 | 23.2 | * |
| total controls | | 12.1 | 12 | ns |

Negative ITEMS

| | | | | |
|---|---|---|---|---|
| Gloomy | QR | 3.3;0.3 | 1.4;0.4 | * |
| | Controls | 3.3;0.4 | 3.2;0.3 | ns |
| Fed up | | 3.1;0.5 | 2;0.4 | * |

|          | | | |
|----------|------|------|----|
|          | 3.3;0.4 | 2.9;0.7 | ns |
| Jittery  | 2.9;0.5 | 2.9;0.6 | ns |
|          | 2.9;0.6 | 3.1;0.5 | ns |
| Drowsy   | 3.1;0.2 | 1;0.4 | * |
|          | 3.3;0.2 | 3.2;0.2 | ns |
| Grouchy  | 3.3;0.4 | 1.1;0.4 | * |
|          | 3.3;0.3 | 3.2;0.4 | ns |
| Sad      | 3.3;0.1 | 1.9;0.5 | * |
|          | 3.4;0.2 | 3;0.6 | ns |
| Tired    | 3.3;0.4 | 2.2;0.4 | * |
|          | 3,1;0.3 | 3.5;0.1 | ns |
| Nervous  | 3.2;0.2 | 1.8;0.4 | * |
|          | 3.3;0.2 | 2.3;0.2 | * |
| Total QR | 25.5 | 14.3 | * |
| Total controls | 25.9 | 24.4 | * |

Table 7

Conclusions:

3 month QR intake in subjects with chronic fatigue syndrome, QR:

- Decreased the free radicals in the plasma proving a potent antioxidant effect
- Statistically improved the fatigue as per the chronic fatigue questionnaire
- Statistically improved the mood as per the BMIS.
- It was also repeatedly reported by the study participants that their sleep patterns and quality of sleep were significantly improved notably by increasing the REM sleep duration.

The invention claimed is:

1. A method for treating a disorder selected from the group consisting of a sleep disorder, an anxiety disorder, and fatigue, the method comprising administering to a subject in need thereof an effective amount of a composition consisting essentially of an extract from a plant of the genus *Quercus* wherein said extract has more than 10% w/w of ellagitannins based on dried extract.

2. The method according to claim 1, wherein said extract comprises Roburins or derivatives thereof.

3. The method of claim 1, wherein the extract is selected from the group consisting of extracts from wood, bark, fruit, roots, or leaves.

4. The method of claim 3, wherein the plant is selected from *Quercus alba, Quercus brutia Tenore, Quercus peduncul iflora, Quercus haas, Quercus petraea* and *Quercus robur* extracts.

5. The method of claim 4, wherein the plant is *Quercus robur*.

6. The method of claim 1, wherein the sleep disorder is insomnia, hypersomnia, sleep rhythm problem, or a sleep-disruptive behavior.

7. The method of claim 1, wherein the fatigue comprises lack of energy, lack of vitality or weakness.

8. The method of claim 7, wherein the treatment of fatigue comprises enhancement of treatment or alleviation of Chronic Fatigue Syndrome (CSF).

9. The method according to claim 1, wherein the composition is in the form of a food preparation, a dietary supplement, a nutraceutical, or a beverage.

10. The method of claim 9, wherein the beverage is an energy drink.

11. The method of claim 1, wherein the composition is in a form adapted for oral administration.

12. A method for improving mood, reducing tension, and raising energy, the method comprising administering to a subject in need thereof an effective amount of a composition consisting essentially of an extract of a plant of the genus *Quercus*, wherein said extract has more than 10% w/w of ellagitannins based on dried extract.

13. The method of claim 12, wherein the improvement of mood comprises enhancement of vigour, alleviation of negative mood, and stimulation of positive mood.

14. The method of claim 13, wherein the improvement of mood comprises enhancement of the treatment or the alleviation of a mood disorder selected among depression and mania.

15. The method of claim 12, wherein the extract is selected from the group consisting of extracts from wood, bark, fruit, roots, or leaves.

16. The method of claim 15, wherein the plant is selected from *Quercus alba, Quercus brutia Tenore, Quercus peduncul iflora, Quercus haas, Quercus petraea* and *Quercus robur* extracts.

17. The method of claim 16, wherein the is plant *Quercus robur*.

* * * * *